United States Patent [19]

Gottlieb et al.

[11] Patent Number: 4,920,097

[45] Date of Patent: Apr. 24, 1990

[54] IMMUNOSUPPRESSOR AND METHOD OF EXTRACTION THEREOF FROM LEUKOCYTES

[75] Inventors: A. Arthur Gottlieb; Robert C. Sizemore; Sudhir K. Sinha, all of New Orleans, La.

[73] Assignee: Imreg, Inc., New Orleans, La.

[21] Appl. No.: 256,581

[22] Filed: Oct. 12, 1988

Related U.S. Application Data

[63] Continuation of Ser. No. 867,564, May 28, 1986, abandoned.

[51] Int. Cl.$^5$ .................... A01N 37/18; A61K 35/14
[52] U.S. Cl. ........................ 514/2; 424/101; 530/829
[58] Field of Search ............ 424/101; 514/2

[56] References Cited

U.S. PATENT DOCUMENTS 4,468,379 8/1984 Gottlieb .............................. 424/101

Primary Examiner—Sam Rosen
Attorney, Agent, or Firm—Richard H. Stern

[57] ABSTRACT

Methods of extracting an immunosuppressor from leukocyte dialysates are disclosed, together with methods for using the immunosuppressor and compositions containing the immunosuppressor.

20 Claims, 1 Drawing Sheet

IMMUNOSUPPRESSOR AND METHOD OF EXTRACTION THEREOF FROM LEUKOCYTES

This is a continuing application based on U.S. Ser. No. 867,564, filed May 28, 1986, now abandoned, and the inventors claim the priority date of such parent application,

BACKGROUND OF THE INVENTION

This invention concerns cell-mediated immunity. A typical manifestation of cell-mediated immunity is the delayed hypersensitivity ("DH") skin reaction. A DH skin reaction is observed when an appropriate antigen is injected subcutaneously. Within 24 to 48 hours, local inflammation (erythema) and a swelling and thickening (induration) are observed in a sensitive individual. The degree of sensitivity may be measured by the size and severity of the reaction. The DH reaction also presents characteristic histological findings—specifically, perivascular infiltration of lymphocytes and monocytes in the inflamed area. The cells seen at the site of a DH reaction are derived from the peripheral blood leukocyte (PBL) population.

The mechanisms of cell-mediated immunity are as yet incompletely understood. It is known that the cells which mediate the response are capable of responding in a variety of ways to a challenge from an antigen. These responses include: proliferation of cells bearing specific sensitivity to a given antigen; the induction and multiplication of cells mediating a variety of immune functions, including antibody production; and reactions against foreign cells (such as pathogens or transplants) and tumors.

The present invention relates to the discovery of (1) a method for extracting a "suppressor" of the immunity system, which is isolated from dialyzed extracts of leukocytes, and (2) the suppressor itself that is so extracted. This suppressor profoundly affects the quality and quantity of cell-mediated immunity responses; is useful in the treatment of a variety of clinical conditions characterized by excessive or undesired reaction to a specific cell or antigen; and is useful in the alleviation of certain allergic conditions.

The term "suppressor," and much of the background relevant to the U.S. Pat. No. 4,468,379, Aug. 28, 1984. The prior art in this field is also discussed in the said '379 patent. That discussion is incorporated herein by reference. For the present purpose, the term suppressor may be considered to mean a substance that when administered to a human or other mammalian subject causes a nonspecific (i.e., not antigen-dependent) lessening of the magnitude or rate of immune system reaction, for example as measured by DH response.

SUMMARY OF THE PRESENT INVENTION

The instant invention relates to the subject matter of the '379 patent in that we herein describe an additional process for the extraction of a different suppressor material, which is hereinafter designated as L-4, and we describe such different suppressor material that can be extracted from leukocyte preparations by such process. A chromatography system of the instant invention uses acetonitrile-trifluoroacetic acid aqueous gradients, and permits the isolation of L-4 suppressor material.

DETAILED DESCRIPTION OF THE PREFERRED EMBODIMENT

Figure 1:
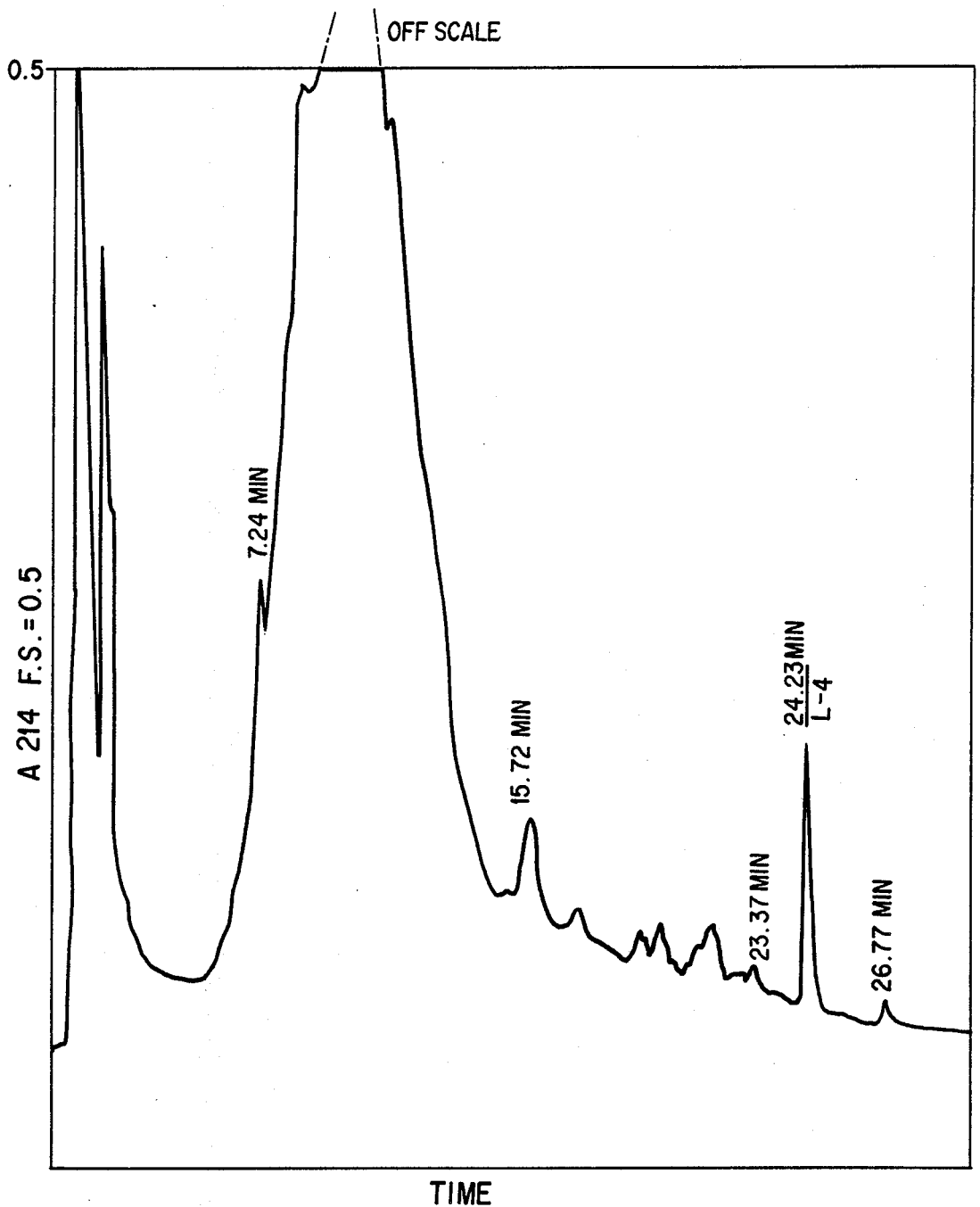
FIG. 1 depicts the elution profile (ultraviolet absorption profile) of the suppressor extracted in the HLPC process described herein.

In the following discussion, procedures are described wherein materials were obtained from human donors and test measurements were made on human recipients. The procedures and reagents used herein were chosen to provide sterile and non-toxic products for human treatment. Despite the toxicity of acetonitrile ($CH_3CN$), the end products of the procedures are nontoxic and they are free of acetonitrile.

Extraction Procedure

The initial step in the preparation of the modulator material of this invention is preparation of leukocyte pellets, followed by separation of the fractions of leukocyte extract of interest herein, viz., those with M.W. between 3500 and 12,000.

EXAMPLE 1—Preparation and Filtration of Leukocyte Extracts

Leukocyte pellets were prepared by the methods of Example 1 of the '379 patent. "L" (or "large" M.W.) fraction of the extract is isolated by passing the material through a filter having a nominal 12,000 M.W. cutoff. The material passed through is then cut off at M.W. >3500 by ultrafiltration or by dialysis in accordance with Example 2 of the '379 patent.

The material with 3500 <M.W. <12,000 is then dried, reconstituted in 0.1% aqueous trifluoroacetic acid, and set aside for the next step.

EXAMPLE 2 —Reverse Phase Liquid Chromatography

Further purification of the material of preceding Example 1 was carried out by reverse-phase high pressure liquid chromatography ("HPLC") on octadecylsilane (ODS). A Novapack C-18 3.9 mm×15 cm column was used with a Waters 680 Series Liquid Chromatograph, but an equivalent instrument made by another manufacturer may be used. The following solvent and gradient system was used, all flow rates 1.0 ml/min:

| Time | % A | % B |
| --- | --- | --- |
| 0 | 10 | 90 |
| 20 | 100 | 0 |
| 30 | 100 | 0 |
| 35 | 10 | 90 |

A fraction eluted at 22.0 to 26.0 minutes, which is designated hereinafter as L-4. It may be recognized by its UV absorption characteristics, which are depicted in FIG. 1. As shown there, the UV absorption profile is plotted on the vertical axis, A 214, Full Scale (F.S.) =0.5 A.U. (Absorbance Units), against time on the horizontal axis, as follows:

During the first 3 to 6 minutes a small number of narrow, high peaks appear, which are not of interest herein. From about 5 to 7 minutes there is a deep trough. At approximately 7 through 15 minutes there is a high, broad peak, which is also not of interest herein except as a marker for L-4, which follows shortly. The next high (approximately 0.1 F.S.) peak is associated with the L-4 suppressor of this invention, and occurs at approximately 24 minutes; it is very narrow (less than 1 minute). Subsequent assay shows suppressor activity of this fraction, which is designated L-4. The material was dried and stored at −70° C.

No immunological activity was found for the materials associated with the other peaks.

Nature of Material of Interest

The foregoing HPLC data makes it possible to characterize the L-4 material of interest with sufficient particularity, for those familiar with this art, to permit repeatable extractions. However, it is not possible as yet to characterize the structure of the molecule or molecules of interest in terms of a chemical formula. Certain physical and chemical features can be inferred, however, from the data.

First, there is some peptide material present in the molecule or molecules of interest, because the particular UV absorption (A214) is typically associated with a peptide bond. Probably, the molecule or molecules of interest are polypeptides with other groups attached. It is uncertain how many peptide groups are involved. The fact that 3500 <M.W. <12,000 indicates the possibility of considerably more peptide groups than the two or three groups present in the inventor Gottlieb's previously disclosed amplifier immunomodulators Tyr-Gly and Tyr-Gly-Gly.

Second, the L-4 material comes off the column in the zone of approximately 80% ±5% acetonitrile concentration. That indicates that the molecule or molecules of interest are relatively hydrophobic, which in turn suggests that the molecule or molecules of interest have a high affinity for a relatively waxy column and probably contain a considerable C or CH component, such as several groups such as $CH_3$, $C_2H_5$, acetyl, COOH, glucose. Because of the high weight, ring groups (e.g., phenyl) should not be excluded from consideration. Of course, since this is a product produced in the human body, the groups must be nontoxic, pharmaceutically acceptable ones or the human body could never have evolved L-4 as a messenger material for maintaining homeostasis in the human immune system.

Based on general information about lymphokines and like biological agents, it is considered that the molecule or molecules of interest probably are essentially polypeptides with added organic constituents attached to at least some of the peptide groups. A possible structure is:

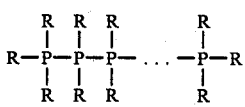

where P is an amino acid group such as Tyr, Gly, etc., and where R is a pharmaceutically acceptable organic group such as acetyl, ethyl, benzyl, etc. (In the diagram, the different P's may be different amino groups and the different R's may be either nulls or different organic groups.) As used hereinafter, the term "essentially consisting of polypeptide material" is intended to refer to molecules like that depicted above, e.g. acetylated and/or methylated and/or ethylated and/or esterified polypeptides.

Further, the foregoing information suggests that it would be appropriate to methylate, ethylate, acetylate, etc. the natural polypeptide material using well known organic chemistry techniques to do so, in order to determine whether the resulting product has improved pharmacological action. It is known that use of molecular modifications of this type may improve blood level, speed of absorption, and other pharmacological parameters. Examples in the literature include the dechlorination of chlortetracycline to produce tetracycline, and the saturation of a carbon bond in chlorothiazide to produce hydrochlorothiazide. It is therefore considered that the scope of the invention includes variations on the polypeptide material of interest described above, where the polypeptide is methylated, acetylated, etc. by devices known to persons of ordinary skill in polypeptide chemistry. In this connection, it is observed that lack of structural knowledge of L-4 beyond that stated above will not prevent persons of ordinary skill in this art to utilize such devices, for it is not necessary to know the exact structure of a polypeptide, for example, to be able to acetylate it.

Demonstration of Suppressor Activity

The L-4 material of Example 2 was tested for suppressor activity by measuring its ability to reverse antigen-induced migration inhibition in a direct leukocyte or macrophage migration inhibition assay. These assays were selected because immunologists regard them as probable indicators of immunosuppressor and/or anti-inflammatory activity in the body.

A sample of the L-4 material of Example 2 was reconstituted with sterile saline and is successively diluted with medium to provide the following preparations:

| Preparation | A | B | C | D | E | F |
|---|---|---|---|---|---|---|
| Dilution (1:—) | 100 | 500 | 1000 | 5000 | 10,000 | 20,000 |

The direct leukocyte migration inhibition (LMI) assay is an in vitro correlate of delayed type hypersensitivity (DH). The LMI assay examines the effect of leukocyte migration inhibitory factor (LIF) on migrating polymorphonuclear cells. The assay is carried out with triplicate samples (if possible; otherwise, duplicate) for each of the above dilutions with and without antigen; in addition, there are controls with and without antigen, which receive no L-4. (Since there are 6 dilutions and 1 control, the total for the triplicate procedure with antigen and without antigen is $3 \times 7 \times 2 = 42$.)

EXAMPLE 3—LMI assay of L-4 a. Preparation of pellets

A gelatin solution of 2% Knox Gelatin in 0.9% NaCl was prepared by heating in a boiling water bath for 10–15 min. The solution was then equilibrated to 37° C.

Whole heparinized peripheral blood from a tetanus toxoid (TT) or PPD sensitive donor was diluted 1:1 (v/v) with the gelatin solution in 50 cc polypropylene tubes and mixed. The tubes were then incubated in a 37° C. incubator for 20 min at a 30° slant and then 10 min upright.

The leukocyte-containing supernatant was transferred to 50 cc polypropylene tubes and centrifuged for 10 min at 1200 rpm, 25° C., to pellet cells.

Each pellet was resuspended in approximately 30 ml Tris-$NH_4Cl$ lysing buffer preequilibrated to 37° C.; the suspension was then incubated at 37° C. for 10 min. In several instances, it was necessary to repeat the lysingincubation step, by combining two pellets in 35 ml of the buffer.

Pellets were pooled in a 15 ml conical tube and were washed twice with cold RPMI-1640 (GIBCO)+10% heat inactivated fetal calf serum (FCS). The material was then centrifuged for 10 min at 1200 rpm, 10° C., to pellet the cells.

b. Preparation of hematocrit tubes

The pellets were resuspended to $4 \times 10^7$/ml in RPMI-1640 +10% FCS +2% PSN (Complete RPMI). The resulting cell suspension was placed in microhematocrit capillary tubes (75 ul)(as used herein, ul =microliter, ug=micrograms), by capillary action. The tubes were plugged with clay (Seal-Ease), which was gently tapped to insure a good seal. The tubes were placed on ice.

The tubes were centrifuged at approximately 800 rpm for 10 min, 10° C.

c. Addition of reagents

Enough tubes were selected to permit triplicate samples for each group in the assay. The assay involves 42 samples for triplicate, or if only duplicate samples can be provided, 28. The control group is Complete RPMI without other reagents.

Each tube was scored with an ampule file at the cell-fluid interface. The tubes were gently broken and positioned in the wells of a 24-well Costar plate, after greasing the plug ends with silicone grease. Each tube was perpendicular to and in contact with the well wall.

Each tube was overlaid with 1 ml Complete RPMI. For the tubes to which antigen was to be added, TT or PPD was also added (TT=100–150 Lf/ml, PPD=75–100 ug/ml). For the tubes to which L-4 was to be added, the appropriate dilution was also added.

The plates were incubated for 16–18 hours at 37° C. to permit leukocyte migration.

d. Measurements and calculations

The plates were each placed on an overhead projector and the migration patterns were projected onto paper, where they were traced. For each fan, two perpendicular diameters were measured. The migration area was calculated for each fan, and groups within the collection were averaged.

The percent migration inhibition (PMI) is defined in terms of the foregoing data. The following parameters are defined in terms of average fan areas (AFA):

A =AFA for culture of antigen +particular L-4 dilution
B =AFA for culture of particular L-4 dilution
C =AFA for culture of antigen
D =AFA for culture of Complete RPMI alone.

The PMI is then defined as:

Experimental PMI =100[1 −(A/B)]
Control PMI =100[1 −(C/D)].

The following percentages of migration inhibition (Table A) were observed for the various preparations:

TABLE A

| PMIs for Various L-4 Dilutions - LIF Assay | |
| --- | --- |
| Preparation | PMI (%) |
| A | 48.69 ± 9.4 |
| B | 21.60 ± 5.8 |
| C | 34.79 ± 1.9 |
| D | 9.32 ± 8.2 |
| E | 46.64 ± 6.4 |
| F | 29.53 ± 6.3 |
| Control | 43.09 ± 2.8 |

The data indicates that addition of L-4 to a direct leukocyte migration inhibition assay resulted in reversal of antigen-induced migration inhibition in a dose-dependent manner. Although the effect depended on concentrations of reagents, it was established that L-4 had no significant effect on leukocyte migration in the absence of antigen. Thus the L-4 suppressed (i.e., reversed) antigen-induced LIF activity.

In addition, an assay was made by measuring macrophage migration inhibition (MMI), using peripheral blood monocytes as indicator cells. The same preparations were used as in Example 3, except that Preparation A was not used.

EXAMPLE 4-MMI assay of L-4

Mononuclear cells were prepared by standard Ficoll-Hypaque density centrifugation of whole blood from an antigen-sensitive donor. To assay 5 dilutions of a test sample, approximately 200–250 ml blood is necessary.

Except for the omission of gelatin solution, pellets were prepared as in Example 3 - §a.

Hematocrit tubes were prepared as in Example 3 - §b, except that the initial resuspension of pellet was to $1 \times 10^8$/ml. The procedures of Example 3 - §§ and d were then followed (without Preparation A).

The PMI data corresponding to that of Example 3 is shown below in Table B.

TABLE B

| PMIs for Various L-4 Dilutions - MMI Assay | |
| --- | --- |
| Preparation | PMIF (%) |
| B | 28.23 ± 10.74 |
| C | 21.30 ± 3.49 |
| D | 30.41 ± 3.90 |
| E | 31.49 ± 8.77 |
| F | 37.91 ± 2.66 |
| Control | 39.15 ± 3.90 |

The data indicates that addition of L-4 to this system also resulted in a dose-dependent reversal of antigen-induced migration inhibition. As in the LMI assay, L-4 had no significant effect in the absence of antigen. Thus, L-4 reversed macrophage inhibition factor (MIF) as well as LIF activity. As indicated above, immunologists regard these in vitro assays as indicators of probable in vivo immunosuppressor and/or anti-inflammatory activity. It is thus seen that L-4 is to be considered a potent immunosuppressor and anti-inflammatory agent, and its use is indicated for conditions in which suppression of immune response is sought, such as in preparing patients to receive organ transplants, contact dermatitis (e.g., poison ivy), and other hyperimmune or autoimmune conditions (e.g., rheumatoid arthritis, lupus, diabetes type I). It may appropriately be administered for this purpose by injection for systemic effects and topically or subcutaneously for local effect.

EXAMPLE 5 - Poison ivy treatment

A patient suffers from erythema and itching resulting from poison ivy. A salve is prepared in a cold cream base, containing a medically predetermined amount (e.g., from approximately 1 ng/ml to approximately 2 ng/ml) of L-4. The salve is applied to the affected skin area every four hours until erythema subsides.

EXAMPLE 6 - Rheumatoid arthritis

A patient suffers from rheumatoid arthritis, which is believed to have a significant autoimmune component.

The patient is given weekly subcutaneous or intradermal injections of 0.1 ml of a preparation containing a medically predetermined amount (e.g., from approximately 10 pg/ml to approximately 20 pg/ml) of L-4 until joint inflammation subsides. After that, the same injections are given biweekly.

EXAMPLE 7 - Lupus

A patient suffers from lupus erythematosis. The patient is given weekly subcutaneous or intradermal injections of 1 ml of a preparation containing an amount of L-4 that the attending physician considers medically appropriate (e.g., approximately 10 pg/ml to approximately 20 pg/ml) for 6 weeks. The attending physician monitors the patient's condition and increases or decreases the dose in accordance with the physician's medical judgment.

It may be considered of scientific interest whether the L-4 suppressor material of the instant invention is a moiety of or is otherwise related to the L-suppressor or S-suppressor materials of Gottlieb U.S. Pat. No. 4,468,379. As indicated above, L-4 suppressor has M.W. between 3500 and 12,000. L-suppressor of the '379 patent has M.W. in the same range, while S-suppressor has M.W. less than 3500. Accordingly, S-suppressor is at the outset ruled out. Several control tests may be used to demonstrate that L-4 is a separate suppressor entity from the L-suppressor of the '379 patent.

EXAMPLE 8 - First Control

L-4 material of Example 2 was loaded onto an HTP column and was subjected to elution with a gradient of ammonium bicarbonate in accordance with the procedure of Example 8 of the '379 patent. Note: The L-suppressor fractions of that procedure elute from the portion of the gradient between 0.1 M and 0.15 M ammonium bicarbonate (see Example 9, '379 patent).

In the instant example, the material that eluted in that particular portion of the gradient was without immunological activity, as measured by the DH assay of Example 9 of the '379 patent. The only material eluting with immunological activity eluted in the portion of the gradient between 0.4 M and 0.5 M; such material was suppressor material, as shown by DH assay, and should be identified with the L-4 material loaded onto the column.

It is considered that this conclusively demonstrates that the L-4 material loaded into the column was not L-suppressor of the '379 patent, because the L-4 material did not elute where any L-suppressor should have eluted if it was present in the material loaded onto the column. That two entities elute from different portions of a gradient demonstrates intrinsic physical and chemical differences between the entities (such as different M.W. and/or different hydrophobicity).

EXAMPLE 9 - Second Control

L-suppressor material of the '379 patent is fluorescently or radioactively tagged and loaded onto the HPLC column of Example 2, above, and is subjected to the HPLC procedure of Example 2.

No peak is observed in the vicinity of 22.0 to 26.0 minutes, and the material that elutes at such portion of the gradient is found to be without immunological activity in a DH assay. Tagged elutant is recovered only in a different part of the gradient.

It is considered that L-suppressor does not contain L-4 suppressor, because of the different elution characteristics of the products.

EXAMPLE 10 - Third Control

The procedure of Example 9, above, is repeated with S-suppressor material of the '379 patent. The same results are observed.

GENERAL CONCLUDING REMARKS

The above described procedures disclose what the inventor believes is a hitherto unknown method of modifying human immune system response. The disclosure also describes hitherto unknown compositions for effecting such immunomodulation, as well as novel extraction procedures for obtaining the desired material in medically (pharmaceutically) acceptable form.

While the invention has been described primarily in connection with a specific and preferred embodiment thereof, it will be understood that it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made.

As used in the claims, the terms dialyze, dialysate, and related words are intended to comprehend equivalent means of separating molecules and the material resulting from such separation, such as by use of ultrafiltration, ultracentrifugation, electrophoresis, and the like. Thus dialysate includes ultrafiltrate. The term size fractionating includes dialyzing, ultrafiltering, and doing like processes.

Dilute aqueous trifluoroacetic acid solution means approximately 0.1% solution.

Chromatogtraphically elutable with a specified solvent and gradient system has the meaning indicated in the '379 patent, column 15. That is, generally speaking, having the property of being able to be eluted by reverse phase HPLC with the specified solvent, usually as specified with greater particularity in terms of the gradient zone in which the material elutes, the particular gradient zone being designated in terms of solvent concentration, refractive index, UV absorption, and/or other characteristics that would permit a person skilled in the art to recognize the zone in question and thus know which elutant to collect. The matrix (such as ODS) may also be specified.

When reference is made to UV absorption profiles, the wavelength in question is approximately 214 nm.

As indicated in the section concerning the nature of the material of interest, following Example 2, the L-4 material described herein may be a single molecular species or a mixture of molecular species. The UV absorption characteristics suggest presence of one or more peptide bonds. Hence, L-4 material may be a polypeptide present in one or more isomeric forms, and present as one or more derivatives of such forms (e.g., esters, amides, acetylated polypeptides). The procedure developed thus far does not permit the inventors to give detailed information about the molecular structure of L-4. However, the available information permits the description of a material that can be reproducibly produced by means of the procedures described in the specification.

Also, the UV profile data associated with the product permits an analytic test of a material to determine whether it is L-4. That is, it is possible to take a material and determine whether it is L-4 by means of the procedure of Example 2. The material is placed in the HPLC system of Example 2, where it may be accompanied by a tracer. If the material of interest elutes at approximately 24 minutes under the HPLC conditions stated in Example 2 (approximately 80% concentration of acetonitrile) and is accompanied by a UV absorption peak of appropriate magnitude, the material is probably L-4. The fact can be confirmed by assay procedures such as those of Example 3.

Accordingly, it is considered that the scope of the invention includes not only the novel extraction procedures described in the specification, but also the peptide material herein designated as L-4. In addition, the invention is considered to include not only the naturally occurring L-4 material, but the same material when methylated, ethylated, acetylated, etc. to produce non-natural but pharmaceutically acceptable alternative molecular species, as described above in the specification preceding Example 3.

We claim:

1. In a method of extracting a suppressor from an extract of leukocytes and purifying it whereby said suppressor is separated from extraneous materials in said extract, comprising the
    (1) size fractionating said extract, thereby producing a first dialysate having a nominal M.W. cutoff of approximately 12,000;
    (2) size fractionating said first dialysate, thereby producing a seond dialysate and a retentate, separated from one another at a nominal M.W. cutoff of approximately 3500;
    (3) applying said retentate to a reverse phase octadecylsilane HPLC column;
    (4) eluting said column with a solvent system;
the improvement comprising: eluting said column with an acetonitrile in dilute aqueous trifluoroacetic acid gradient, said gradient including a range of acetonitrile concentration from approximately 70% to approximately 80%, thereby producing elutants associated with different portions of said gradient; and collecting the elutant associated with the zone of said gradient wherein acetonitrile concentration is between approximately 75% and approximately 80%, whereby material designated herein as L-4 suppressor is provided.

2. The process of claim 1 wherein the elutant collected is further characterized in terms of its UV absorption profile as being associated with a high narrow peak that is
    the highest peak following a broad higher peak that follows a deep trough,
    less than a quarter the height of said broad higher peak, and
    higher than any subsequent peak;
and said elutant is further characterized by showing suppressor immunomodulatory activity in a leukocyte migration inhibition assay and in a macrophage migration inhibition assay.

3. The product of the process of claim 1.

4. The product of the process of claim 2.

5. A material having a M.W. between 3500 and 12,000, and further characterized by having the following properties:
    (a) being substantially entirely chromatographically elutable from octadecylsilane by acetonitrile in dilute aqueous trifluoroacetic acid gradient, in the portions of said gradient between approximately 70% and approximately 85% acetonitrile concentration;
    (b) being substantially not so elutable in the portions of said gradient below approximately 70% acetonitrile concentration; and
    (c) being substantially free of material that is so elutable below said concentration and of material that is so elutable only above 90% acetonitrile concentration;
    (d) not being chromotographically elutable from hydroxylapatite by aqueous ammonium bicarbonate gradient, in the portions of said gradient between approximately 0.1 M and 0.15 M; and
    (e) nonspecifically causing a lessening of the magnitude or rate of an immune system reaction when administered to a human or other mammalian subject.

6. Material of claim 5 further characterized by the presence of at least one peptide bond, the absence of pharmaceutically unacceptable contaminants, and the abilities to inhibit leukocyte migration and inhibit macrophage migration.

7. Material of claim 6 essentially consisting of polypeptide material.

8. Material of claim 5 further characterized by being, when said material is chromatographically eluted from a dialysed human leukocyte extract with an HPLC system comprising an acetonitrile in dilute aqueous trifluoroacetic acid gradient and when elutants of said chromatographic system are monitored for UV absorption, associated with a high narrow UV absorption peak that is:
    the highest peak following a broad higher peak that follows a deep trough,
    less than a quarter the height of said broad high peak, and
    higher than any subsequent peak.

9. A composition comprising material of claim 5, in a pharmaceutically acceptable vehicle, free of pyrogens and other pharmaceutically unacceptable products, and in a dosage amount effective to cause a lessening of a human immune system reaction.

10. A method of decreasing the speed or magnitude of a person's immune system response comprising administration to said person of an effective dosage amount of material of claim 5.

11. The method of claim 10 wherein the person suffers from and is treated for an autommimune or hyperimmune condition.

12. The method of claim 11 wherein said person suffers from and is treated for rheumatoid arthritis.

13. The method of claim 11 wherein said person suffers from and is treated for diabetes type I.

14. The method of claim 11 wherein said person suffers from and is treated for systemic lupus erythematosus.

15. The method of claim 10 wherein said person suffers from and is treated for contact dermatitis.

16. The method of claim 15 wherein said contact dermatitis is caused by posion ivy, oak, or sumac.

17. The method of claim 10 wherein said person requires an organ transplant and is treated to suppress rejection.

18. Material of claim 6 combined with at least one pharmaceutically acceptable organic group having 1-6 carbon atoms to form an alkyl or ester derivative, and accompanied by a pharamceutically acceptable carrier.

19. The product of claim 18 wherein said group is selected from the group consisting of methyl, ethyl, and acetyl.

20. Material of claim 6 in the form of a benzyl derivative, and accompanied by a pharmaceutically acceptable carrier.

* * * * *